United States Patent
DiGrazia et al.

(10) Patent No.: US 10,209,170 B2
(45) Date of Patent: Feb. 19, 2019

(54) METER ELECTRONICS AND METHOD FOR OBTAINING FLOW FLUID VISCOSITY AT A REFERENCE TEMPERATURE

(71) Applicant: Micro Motion, Inc., Boulder, CO (US)

(72) Inventors: Xiaoling DiGrazia, Longmont, CO (US); Ruth Scott, Lafayette, CO (US)

(73) Assignee: Micro Motion, Inc., Boulder, CO (US)

( * ) Notice: Subject to any disclaimer, the term of this patent is extended or adjusted under 35 U.S.C. 154(b) by 300 days.

(21) Appl. No.: 14/426,309

(22) PCT Filed: Sep. 27, 2012

(86) PCT No.: PCT/US2012/057475
§ 371 (c)(1),
(2) Date: Mar. 5, 2015

(87) PCT Pub. No.: WO2014/051582
PCT Pub. Date: Apr. 3, 2014

(65) Prior Publication Data
US 2015/0204769 A1    Jul. 23, 2015

(51) Int. Cl.
*G01N 11/02* (2006.01)
*G01N 11/16* (2006.01)
(Continued)

(52) U.S. Cl.
CPC ............ *G01N 11/02* (2013.01); *G01N 11/16* (2013.01); *G01N 29/02* (2013.01); *G01N 2011/0013* (2013.01)

(58) Field of Classification Search
CPC ........... G01N 11/16; G01N 2011/0013; G01N 29/02; G01N 11/02; G01N 11/00;
(Continued)

(56) References Cited

U.S. PATENT DOCUMENTS

| 5,359,881 A | 11/1994 | Kalotay et al. |
| 5,861,561 A | 1/1999 | Van Cleve et al. |

(Continued)

FOREIGN PATENT DOCUMENTS

| EP | 0233408 A2 | 12/1987 |
| GB | 736204 | 9/1955 |

(Continued)

OTHER PUBLICATIONS

Irina Nita, Study of Density and Viscosity variation with temperature for fuels used for Diesel engine,Nov. 1, 2011, vol. 22, No. 1, pp. 57-61.*

(Continued)

*Primary Examiner* — Randy Gibson
*Assistant Examiner* — Gedeon M Kidanu
(74) *Attorney, Agent, or Firm* — The Ollila Law Group LLC (57) ABSTRACT

Meter electronics (20) and method for obtaining a flow fluid viscosity at a predetermined reference temperature are provided. The meter electronics (20) includes an interface (201) configured to exchange communications, a storage system (204) configured to store a predetermined reference temperature (211), a measured fluid viscosity (214), a measured fluid temperature (215), and a temperature-viscosity relational data (218) that relates temperature to viscosity over a predetermined range of flow fluid temperatures, and a processing system (203) coupled to the interface (201) and to the storage system (204), with the processing system (203) configured to obtain the measured fluid temperature (215), obtain the measured fluid viscosity (214), and generate a reference temperature viscosity (227) using the measured fluid viscosity (214) and the temperature-viscosity relational data (218), with the generated reference temperature viscos- (Continued)

ity (227) corresponding to the predetermined reference temperature (211).

18 Claims, 8 Drawing Sheets

(51) Int. Cl.
*G01N 29/02* (2006.01)
*G01N 11/00* (2006.01)

(58) Field of Classification Search
CPC ............ G01N 2009/006; G01F 1/8413; G01F 1/8477; G01F 1/8495; G01F 15/022; G01F 1/8404; G01F 5/00
USPC ........ 73/54.01–54.02, 861.355; 702/50, 100; 703/2
See application file for complete search history.

(56) References Cited

U.S. PATENT DOCUMENTS

| | | | |
|---|---|---|---|
| 5,877,409 A * | 3/1999 | Girling | G01N 33/2829 73/54.06 |
| 2002/0080362 A1 * | 6/2002 | Behroozi | G01N 11/00 356/477 |
| 2008/0184813 A1 | 8/2008 | Patten et al. | |
| 2008/0228424 A1 * | 9/2008 | Grosser | G01N 11/08 702/100 |
| 2009/0120169 A1 | 5/2009 | Chandler et al. | |
| 2010/0039109 A1 * | 2/2010 | Cheng | G01N 11/00 324/303 |
| 2010/0089174 A1 | 4/2010 | Van Cleve | |
| 2012/0083915 A1 * | 4/2012 | Allan | G01N 11/00 700/104 |

FOREIGN PATENT DOCUMENTS

| | | | |
|---|---|---|---|
| GB | 762824 | 12/1956 | |
| GB | 2259368 A * | 3/1993 | ............... G01N 9/00 |
| JP | 5-113395 A | 5/1993 | |
| JP | 2005-345213 A | 12/2005 | |
| RU | 2221999 C2 | 1/2004 | |
| WO | 2005103645 A2 | 11/2005 | |

OTHER PUBLICATIONS

Ioana Stanciu: "A new viscosity-temperature relationship for vegetable oil", Journal of Petroleum Technology and Alternative Fuels, vol. 3, No. 2, Feb. 29, 2012 pp. 19-23, XP055069387, doi:10.5897/JPTAF12.001 paragraph "Results and Discussion".

Irina Nita Et Al: "Study of density and viscosity variation with teperature for fuels used for Diesel engin", Ovidius University Annals of Chemistry, Nov. 30, 2011 pp. 57-61, XP055069417, Retrieved From the Internet: URL:http://anale-chimie.univ-ovidius.ro/anale-chimie/chemistry/2011-1/full/10_nita.pdf.

* cited by examiner

METER ELECTRONICS AND METHOD FOR OBTAINING FLOW FLUID VISCOSITY AT A REFERENCE TEMPERATURE

BACKGROUND OF THE INVENTION

1. Field of the Invention

The present invention relates to a meter electronics and method for obtaining a flow fluid viscosity, and more particularly, to a meter electronics and method for obtaining a flow fluid viscosity at a predetermined reference temperature.

2. Statement of the Problem

Vibratory sensors, such as vibratory densitometers and vibratory viscometers, typically operate by detecting motion of a vibrating element that vibrates in the presence of a fluid material to be measured. Properties associated with the fluid material, such as density, viscosity, temperature, and the like, can be determined by processing measurement signals received from motion transducers associated with the vibrating element. The vibration modes of the vibrating element system generally are affected by the combined mass, stiffness and damping characteristics of the vibrating element and the fluid material.

In addition to directly measuring viscosity of process fluid at process temperature, refinery applications may require the capability to determine the viscosity at a reference temperature, as the fluid viscosity may change with temperature. The sensitivity of viscosity to temperature with some fluids may be higher than with other fluids.

The ASTM D341 standard, using the interpolation function of Ubbelohde-Walther, has been widely adopted for ascertaining the kinematic viscosity of a petroleum oil or liquid hydrocarbon at any temperature within a limited range. The ASTM D341 equation has two constants A and B that must be found before viscosity can be calculated at the reference temperature. The ASTM D341 equation, as a mathematical model to describe temperature viscosity behavior, is especially suitable for hydrocarbon fluids or mixtures.

One prior art method for calculating a reference temperature viscosity employs the ASTM D341 equation along with a dual viscometer including a heat exchanger. The dual viscometer measures the viscosity of a process fluid at two different temperatures and thereby determines the constants A and B. The viscosity can then be calculated for intermediate temperatures using the two constants.

The prior art dual viscometer and heat exchanger approach has disadvantages, however. The prior art dual viscometer and heat exchanger approach is complex. The heat exchanger may require additional space.

The prior art dual viscometer and heat exchanger approach is expensive. The cost of a dual viscometer and heat exchanger, and the installation cost, may be too great to justify in some applications.

ASPECTS OF THE INVENTION

In one aspect of the invention, a meter electronics for obtaining a flow fluid viscosity at a predetermined reference temperature comprises:
  an interface configured to exchange communications;
  a storage system configured to store a predetermined reference temperature, a measured fluid viscosity, a measured fluid temperature, and a temperature-viscosity relational data that relates temperature to viscosity over a predetermined range of flow fluid temperatures; and
  a processing system coupled to the interface and to the storage system, with the processing system configured to obtain the measured fluid temperature, obtain the measured fluid viscosity, and generate a reference temperature viscosity using the measured fluid viscosity and the temperature-viscosity relational data, with the generated reference temperature viscosity corresponding to the predetermined reference temperature.

Preferably, the temperature-viscosity relational data relates temperature to viscosity for two or more flow fluids over a predetermined range of flow fluid temperatures.

Preferably, one or both of the measured fluid viscosity and the measured fluid temperature are obtained using a vibratory sensor.

Preferably, the temperature-viscosity relational data comprises a polynomial equation.

Preferably, the temperature-viscosity relational data comprises a polynomial equation of a predetermined polynomial order.

Preferably, the temperature-viscosity relational data comprises a relational expression stored as a mathematical equation.

Preferably, the temperature-viscosity relational data comprises a relational expression stored as a data structure.

Preferably, the storage system stores two or more reference flow fluid curves and a predetermined polynomial order, with the processing system being configured to obtain the predetermined polynomial order and create the temperature-viscosity relational data from the two or more reference flow fluid curves, the measured fluid temperature, the predetermined reference temperature, and the predetermined polynomial order.

In one aspect of the invention, a method of obtaining a flow fluid viscosity at a predetermined reference temperature comprises:
  obtaining a measured fluid temperature;
  obtaining a measured fluid viscosity; and
  generating a reference temperature viscosity using the measured fluid viscosity and a temperature-viscosity relational data that relates temperature to viscosity over a predetermined range of flow fluid temperatures, with the generated reference temperature viscosity corresponding to the predetermined reference temperature.

Preferably, the temperature-viscosity relational data relates temperature to viscosity for two or more flow fluids over a predetermined range of flow fluid temperatures.

Preferably, one or both of the measured fluid viscosity and the measured fluid temperature are obtained using a vibratory sensor.

Preferably, the temperature-viscosity relational data comprises a polynomial equation.

Preferably, the temperature-viscosity relational data comprises a polynomial equation of a predetermined polynomial order.

Preferably, the temperature-viscosity relational data comprises a relational expression stored as a mathematical equation.

Preferably, the temperature-viscosity relational data comprises a relational expression stored as a data structure.

Preferably, the temperature-viscosity relational data is generated from two or more reference flow fluid curves using curve fitting.

Preferably, the method further comprises the preliminary steps of obtaining a predetermined polynomial order to be used and creating the temperature-viscosity relational data from two or more reference flow fluid curves, the measured fluid temperature, the predetermined reference temperature, and the predetermined polynomial order.

Preferably, the method further comprises the preliminary steps of measuring viscosity of a particular flow fluid at two or more temperatures to create two or more temperature-viscosity data points for the particular flow fluid, processing two or more flow fluids and accumulating a plurality of temperature-viscosity data points for the two or more flow fluids to create two or more flow fluid curves, obtaining a predetermined polynomial order to be used, and creating the temperature-viscosity relational data from the two or more reference flow fluid curves, the measured fluid temperature, the predetermined reference temperature, and the predetermined polynomial order.

DESCRIPTION OF THE DRAWINGS

The same reference number represents the same element on all drawings. The drawings are not necessarily to scale.

DETAILED DESCRIPTION OF THE INVENTION

FIGS. 1-8 and the following description depict specific examples to teach those skilled in the art how to make and use the best mode of the invention. For the purpose of teaching inventive principles, some conventional aspects have been simplified or omitted. Those skilled in the art will appreciate variations from these examples that fall within the scope of the invention. Those skilled in the art will appreciate that the features described below can be combined in various ways to form multiple variations of the invention. As a result, the invention is not limited to the specific examples described below, but only by the claims and their equivalents.

Figure 1:
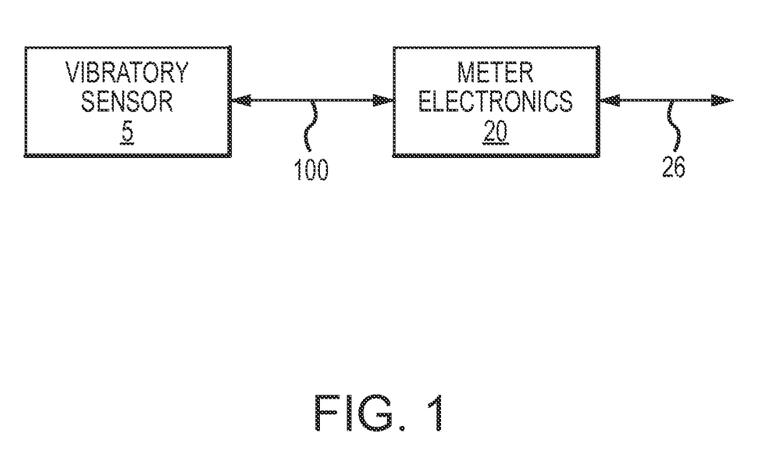
FIG. 1 shows a vibratory sensor according to the invention.

FIG. 1 shows a vibratory sensor 5 according to the invention. The vibratory sensor 5 may be coupled to a meter electronics 20 by a lead or leads 100. The vibratory sensor 5 and the meter electronics 20 may operate to provide fluid measurements. The vibratory sensor 5 and meter electronics 20 may provide fluid measurements including one or more of a fluid density and a fluid viscosity for a fluid, including flowing or non-flowing fluids. Viscosity is a measure of the resistance of a liquid to flow. Viscosity measurement may comprise an important fluid measurement in the field of industrial process control and OEM applications. A typical vibratory viscosity meter operates on the vibrating element principle. The vibratory sensor 5 and meter electronics 20 may additionally provide fluid measurements including a fluid mass flow rate, a fluid volume flow rate, and/or a fluid temperature. This listing is not exhaustive and the vibratory sensor 5 may measure or determine other fluid characteristics.

The fluid can comprise a liquid. The fluid can comprise a gas. Alternatively, the fluid can comprise a multi-phase fluid, such as a liquid that includes entrained gas, entrained solids, multiple liquids, or combinations thereof.

The vibratory sensor 5 may be mounted in a pipe or conduit. The vibratory sensor 5 may be mounted in a tank or container or structure for holding a fluid. The vibratory sensor 5 may be mounted in a manifold or similar structure for directing a fluid flow.

In some embodiments, the vibratory sensor 5 may comprise a vibratory tine sensor. Alternatively, in other embodiments the vibratory sensor 5 may comprise a vibratory conduit sensor. In some embodiments, the vibratory sensor 5 may comprise a vibratory densitometer 5 or a vibratory viscometer 5. Alternatively, the vibratory sensor 5 may comprise a Coriolis mass flow meter 5.

The meter electronics 20 may provide electrical power to the vibratory sensor 5 via the lead or leads 100. The meter electronics 20 may control operation of the vibratory sensor 5 via the lead or leads 100. For example, the meter electronics 20 may generate a drive signal and supply the drive signal to the vibratory sensor 5, wherein the vibratory sensor 5 generates a vibration in one or more vibratory components using the drive signal. The drive signal may control the vibrational amplitude. The drive signal may control the vibrational frequency. The drive signal may control the vibrational duration and/or vibrational timing.

The meter electronics 20 may receive a measurement signal or signals from the vibratory sensor 5 via the lead or leads 100. The meter electronics 20 may be further coupled to a communication path 26. The meter electronics 20 may communicate a measurement signal or signals over the communication path 26. The meter electronics 20 may process the received measurement signal or signals to generate a measurement value or values and may communicate a measurement value or values over the communication path 26.

In addition, the meter electronics 20 may receive information over the communication path 26. The meter electronics 20 may receive commands, updates, operational values or operational value changes, and/or programming updates or changes over the communication path 26.

The meter electronics 20 may process a measurement signal or signals to determine a frequency of the signal or signals. The frequency may comprise a resonant frequency of the fluid. The frequency may be used to determine a density of the fluid. Further, or in addition, the meter electronics may process a measurement signal or signals to determine other characteristics of the fluid, such as a phase shift between signals that can be processed to determine a fluid flow rate, for example. Other vibrational response characteristics and/or fluid measurements are contemplated and are within the scope of the description and claims.

Figure 2:
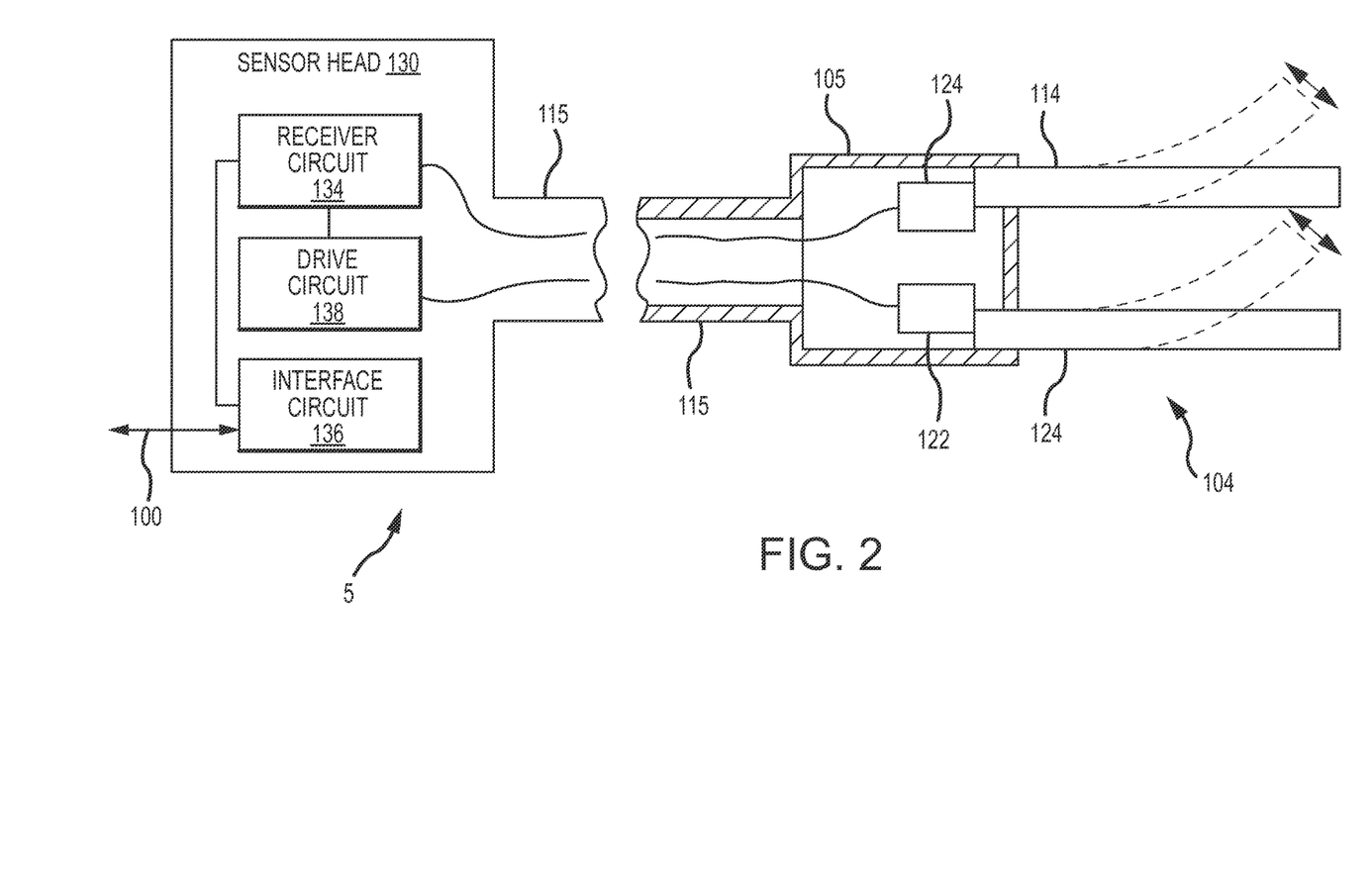
FIG. 2 shows a vibratory tine sensor according to an embodiment of the invention.

FIG. 2 shows a vibratory tine sensor 5 according to an embodiment of the invention. The vibratory tine sensor 5 in the embodiment shown comprises a sensor head 130 that is coupled to a tuning fork structure 104 by a shaft 115. The shaft 115 may be of any desired length. The shaft 115 may be at least partially hollow and wires or other conductors may extend between the sensor head 130 and the tuning fork structure 104 through the shaft 115.

The sensor head 130 may include circuit components such as a drive circuit 138, a receiver circuit 134, and an interface circuit 136 in the embodiment shown. The interface circuit 136 may be coupled to the lead or leads 100 to the meter electronics 20. It should be understood that any or all of the circuit components of the sensor head 130 may be alternatively located in the meter electronics 20.

The vibratory element of the vibratory tine sensor 5 comprises a tuning fork structure 104 which is immersed in a liquid being measured. The tuning fork structure 104 includes a housing 105 that may be affixed to another structure, such as a pipe, conduit, tank, receptacle, manifold, or any other fluid-handling structure. The housing 105 retains the tuning fork structure 104, while the tuning fork structure 104 remains at least partially exposed. The tuning fork structure therefore is configured to be immersed in the fluid.

The tuning fork structure 104 includes first and second tines 112 and 114 that are configured to extend at least partially into the fluid. The first and second tines 112 and 114 comprise elongate elements that may have any desired cross-sectional shape. The first and second tines 112 and 114 may be at least partially flexible or resilient in nature.

The vibratory tine sensor 5 further includes corresponding first and second piezo elements 122 and 124 that comprise piezo-electric crystal elements. The first and second piezo elements 122 and 124 are located adjacent to the first and second tines 112 and 114, respectively. The first and second piezo elements 122 and 124 are configured to contact and mechanically interact with the first and second tines 112 and 114.

The first piezo element 122 may contact at least a portion of the first tine 112. The first piezo element 122 may be electrically coupled to a drive circuit 138, with the drive circuit 138 providing a time-varying drive signal to the first piezo element 122. The first piezo element 122 may expand and contract when subjected to the time-varying drive signal. As a result, the first piezo element 122 may alternatingly deform and displace the first tine 112 from side to side in a vibratory motion (see dashed lines), disturbing the fluid.

The second piezo element 124 may be coupled to a receiver circuit 134 that produces a time-varying response signal corresponding to the deformations of the second tine 114 in the fluid. Movement of the second tine 114 may therefore cause a corresponding electrical vibrational measurement signal to be generated by the second piezo element 124. The second piezo element 124 transmits the vibrational measurement signal to the receiver circuit 134. The receiver circuit 134 may process the vibrational measurement signal signal in some embodiments. The resulting frequency of oscillation is detected by the receiver circuit 134.

The receiver circuit 134 may be coupled to an interface circuit 136. The interface circuit 136 may be configured to communicate with external devices, such as the meter electronics 20. The interface circuit 136 may be configured to communicate the vibrational measurement signal and/or the processed result values. It should be understood that alternatively the meter electronics 20 may process the vibrational measurement signal and/or generate a detected vibrational frequency of the fluid.

The tuning fork structure 104 is generally maintained at a first natural resonant frequency in some embodiments, as modified by the surrounding fluid. The tuning fork structure 104 is typically maintained at the first natural resonant frequency by the drive circuit 138. The drive circuit 138 may receive the vibrational measurement signal from the receiver circuit 134 (or may directly receive the vibrational measurement signal).

The drive circuit 138 may generate a drive signal from the vibrational measurement signal, and may modify characteristics of the vibrational measurement signal in order to generate the drive signal. The drive circuit 138 may modify the vibrational measurement signal to produce a desired resultant frequency disturbance in the fluid. The drive circuit 138 further may modify the vibrational measurement signal to compensate for the length of the wiring between the sensor head 130 and the tuning fork structure 104 and/or to compensate for other losses in the vibrational measurement signal, for example.

Figure 3:
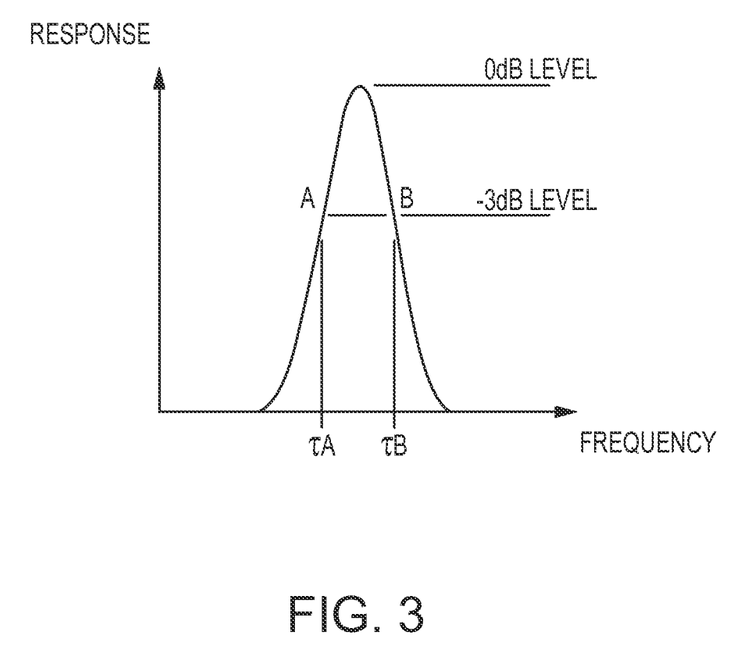
FIG. 3 is a graph of a frequency response curve of a tuning fork structure of FIG. 2.

FIG. 3 is a graph of a frequency response curve of the tuning fork structure 104. The drive circuit 138 may be configured to excite the tuning fork structure 104 into a desired vibration or vibrations. The tuning fork structure 104 may be excited into vibrating at a desired phase shift or phase shifts between the vibration sensor and the vibration driver, producing a vibrational response curve, as shown. The vibrational response curve may be used to characterize the fluid.

The two points A and B may comprise −3 dB points that are 3 dB (decibels) below the amplitude of the peak or resonant vibrational frequency amplitude. Alternatively, the points A and B may comprise predetermined phase offsets, such as −45 and +45 degree phase offsets, for example.

The resonant frequency of the fluid may be determined from the point B, in some embodiments. The resonant frequency is a function of the overall mass of the tine element and the density of the fluid surrounding it. Hence, as the density of the fluid changes, the overall vibrating mass changes, and with it the frequency of point B on the curve. By determining the frequency of point B, and the period $\tau_B$ of the wave at point B (where $\tau$ is approximately $\tau=1/f$), the density of the liquid can be calculated in some embodiments. The point B may be relatively unaffected by the density of the fluid. Alternatively, the vibrational response curve may be assumed to be substantially symmetric and the resonant frequency $f_0$ may be considered to be the midpoint between points A and B.

By determining wave periods for the points A and B of the graph (i.e., the wave periods $\tau_A$ and $\tau_B$), the quality factor (Q) for the fluid can be calculated. The quality factor (Q) may comprise the determined resonant frequency $f_0$ divided by the difference or distance between the points A and B.

The quality factor (Q) may be defined as a measure of the rate at which a vibrating system dissipates its energy. A higher Q indicates a lower rate of energy dissipation. Therefore, the quality factor (Q) of the tuning fork structure 104 is a function of the damping of the tine material and the damping imposed by the viscosity of the surrounding fluid. Hence, as the viscosity of the fluid changes, the overall damping forces change, and with it the Q value.

A viscosity value for the fluid may be determined from the quality factor (Q), where a difference in frequency/wave period ($\tau$) between the points A and B may be related to damping due to the fluid.

Figure 4:
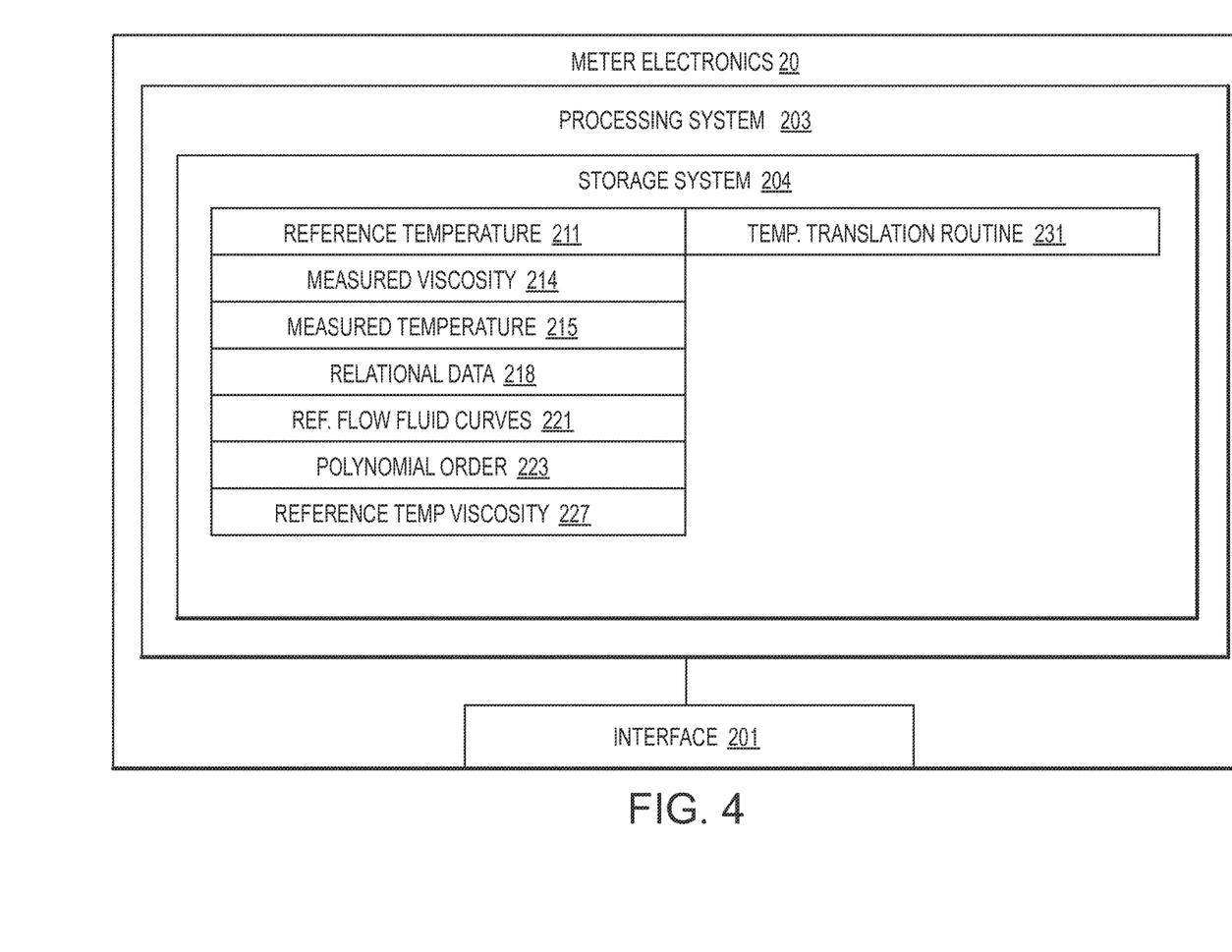
FIG. 4 shows meter electronics of the vibratory sensor for obtaining a flow fluid viscosity at a predetermined reference temperature according to an embodiment of the invention.

FIG. 4 shows meter electronics 20 of the vibratory sensor 5 for obtaining a flow fluid viscosity at a predetermined reference temperature according to an embodiment of the invention. The meter electronics 20 can comprise a component of the vibratory sensor 5. Alternatively, the meter electronics 20 may be coupled to the vibratory sensor 5 or to the flowmeter assembly 10.

The meter electronics 20 can include an interface 201 and a processing system 203. The meter electronics 20 receives first and second sensor signals from the meter assembly 10, such as pickoff/velocity sensor signals and a temperature signal, for example. The meter electronics 20 processes the received signals in order to obtain flow characteristics of the flow material flowing through the meter assembly 10. For example, the meter electronics 20 can determine one or more of a phase difference, a frequency, a time difference ($\Delta t$), a density, a mass flow rate, a volume flow rate, and a viscosity from the sensor signals, for example. In addition, other flow characteristics can be determined according to the invention.

The interface 201 receives the sensor signals from one of the velocity sensors 105a and 105b via the leads 100 of FIG. 1. The interface 201 can perform any necessary or desired signal conditioning, such as any manner of formatting, amplification, buffering, etc. Alternatively, some or all of the signal conditioning can be performed in the processing system 203.

In addition, the interface 201 can enable communications between the meter electronics 20 and external devices, such as through the communication path 26, for example. The interface 201 can be capable of any manner of electronic, optical, or wireless communication.

The interface 201 in one embodiment includes a digitizer (not shown), wherein the sensor signal comprises an analog sensor signal. The digitizer samples and digitizes the analog sensor signal and produces a digital sensor signal. The interface/digitizer can also perform any needed decimation, wherein the digital sensor signal is decimated in order to reduce the amount of signal processing needed and to reduce the processing time.

The processing system 203 conducts operations of the meter electronics 20 and processes flow measurements from the flow meter assembly 10. The processing system 203 executes one or more processing routines and thereby processes the flow measurements in order to produce one or more flow characteristics.

The processing system 203 can comprise a general purpose computer, a microprocessing system, a logic circuit, or some other general purpose or customized processing device. The processing system 203 can be distributed among multiple processing devices. The processing system 203 can include any manner of integral or independent electronic storage medium, such as the storage system 204.

The storage system 204 may be coupled to the processing system 204 or may comprise a portion of the processing system 203. The storage system 204 can store flow meter parameters and data, software routines, constant values, and variable values.

The storage system 204 may store routines that are executed by the processing system 203. In one embodiment, the storage system 204 stores a temperature translation routine 231, for example, that operates to obtain a flow fluid viscosity at a predetermined reference temperature. It should be understood that additional routines may be stored in the storage system 204.

The storage system 204 may store measurements and other data generated by the vibratory sensor 5. The storage system 204 may store a measured fluid viscosity 214 and a measured fluid temperature 215. The measured fluid viscosity 214 and the measured fluid temperature 215 may be generated or obtained by the vibratory sensor 5, for example.

It should be understood that additional measurements or sensor-generated values may be stored in the storage system 204.

The storage system 204 may store data to be used in processing/operation. The storage system 204 in one embodiment stores measurement signals such as the two or more vibrational responses (not shown) received from the velocity/pickoff sensors 105a and 105b. The storage system 204 may store a predetermined reference temperature 211. The storage system 204 may store temperature-viscosity relational data 218, such as temperature-viscosity relational data 218 that may be used to translate viscosity measurements.

The temperature-viscosity relational data 218 in some embodiments relates temperature to viscosity over a predetermined range of flow fluid temperatures. The temperature-viscosity relational data 218 in some embodiments relates temperature to viscosity for two or more flow fluids over a predetermined range of flow fluid temperatures. The temperature-viscosity relational data 218 in some embodiments comprises a polynomial equation. The temperature-viscosity relational data 218 in some embodiments comprises a polynomial equation of the predetermined polynomial order 223. The temperature-viscosity relational data 218 in some embodiments comprises a relational expression stored as a mathematical equation. The temperature-viscosity relational data 218 in some embodiments comprises a relational expression stored as a data structure.

The storage system 204 may store two or more reference flow fluid curves 221, where the two or more reference flow fluid curves 221 reflect temperature-viscosity relationships for two or more flow fluids over a predetermined range of flow fluid temperature. The storage system 204 may store a predetermined polynomial order 223. It should be understood that additional operational data may be stored in the storage system 204.

The storage system 204 may store data that is generated by processing operations. The storage system 204 may store a reference temperature viscosity 227 that is generated from the measured fluid viscosity 214 using the temperature-viscosity relational data 218, for example. It should be understood that additional generated data may be stored in the storage system 204.

In operation, the processing system 203 may retrieve and execute the temperature translation routine 231. As a result, the processing system 203 may obtain the measured fluid temperature 215, obtain the measured fluid viscosity 214, and generate a reference temperature viscosity 227 using the measured fluid viscosity 214 and the temperature-viscosity relational data 218, with the generated reference temperature viscosity 227 corresponding to the predetermined reference temperature 211.

In addition, in some embodiments the storage system 204 may store the two or more reference flow fluid curves 221 and a predetermined polynomial order 223, with the processing system 203 being configured to obtain the predetermined polynomial order 223 and create the temperature-viscosity relational data 218 from the two or more reference flow fluid curves 221, the measured fluid temperature 215, the predetermined reference temperature 211, and the predetermined polynomial order 223.

The reference temperature viscosity 223 may be stored in the storage system 204. The reference temperature viscosity 223 may be accumulated in the storage system 204. The reference temperature viscosity 223 may be transferred or communicated to external devices or locations via the communication path 26 (see FIG. 1).

The vibratory sensor 5 therefore may comprise a single viscometer that employs a multi-curve method to calculate a fluid viscosity, but at a reference temperature instead of at a measured fluid temperature. The meter electronics 20 may hold a pre-defined set of reference viscosity curves (i.e., the two or more reference flow fluid curves 221).

Figure 5:
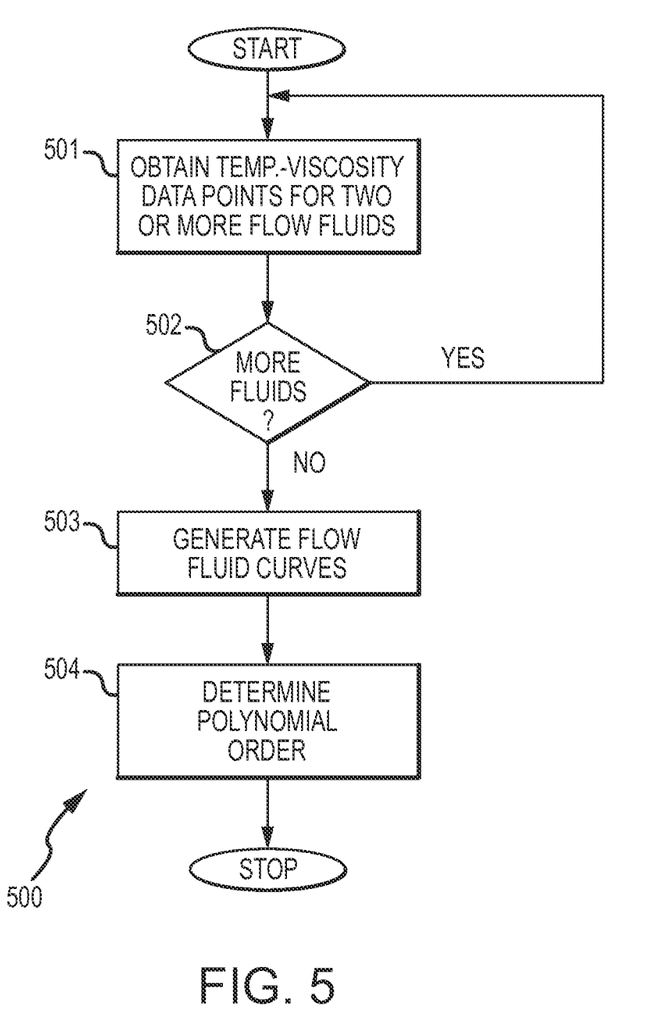
FIG. 5 is a flowchart of a method of generating temperature-viscosity relational data according to an embodiment of the invention.

FIG. 5 is a flowchart 500 of a method of generating temperature-viscosity relational data according to an embodiment of the invention. In step 501, two or more temperature-viscosity data points are obtained for a particular flow fluid (i.e., a particular reference flow fluid). It should be understood that more than two temperature-viscosity data points may be employed, if desired, as a greater number of data points may increase the accuracy or preciseness of the resulting curve. The two or more temperature-viscosity data points are obtained at different flow fluid temperatures. Preferably, the two or more temperature-viscosity data points are obtained at significantly different flow fluid temperatures. It should be understood that the reference fluids do not have to be the same as a flow fluid to be measured in actual operation.

In step 502, it is determined whether there are still flow fluids remaining to be characterized. At least two flow fluids are characterized in order to provide the temperature-viscosity relational data. If more flow fluids remain to be characterized, then the method loops back to step 502 and a next flow fluid is characterized. Otherwise, the method proceeds to step 504.

In step 503, the temperature-viscosity data points for the two or more reference flow fluids are processed in order to generate two or more corresponding reference flow fluid curves. A reference flow fluid curve is generated for each reference flow fluid. Characterization of a large number of reference flow fluids, and the production of a large number of reference flow fluid curves, will generally give a better, more accurate result.

An appropriate curve-fitting technique may be used to generate a representative curve for each reference flow fluid, using the two or more obtained temperature-viscosity data points. The curve-fitting technique may be applied to the temperature-viscosity data points for each reference flow fluid in order to generate the corresponding reference flow fluid curve. This process is repeated for each reference flow fluid in order to generate two or more reference flow fluid curves.

Figure 6:
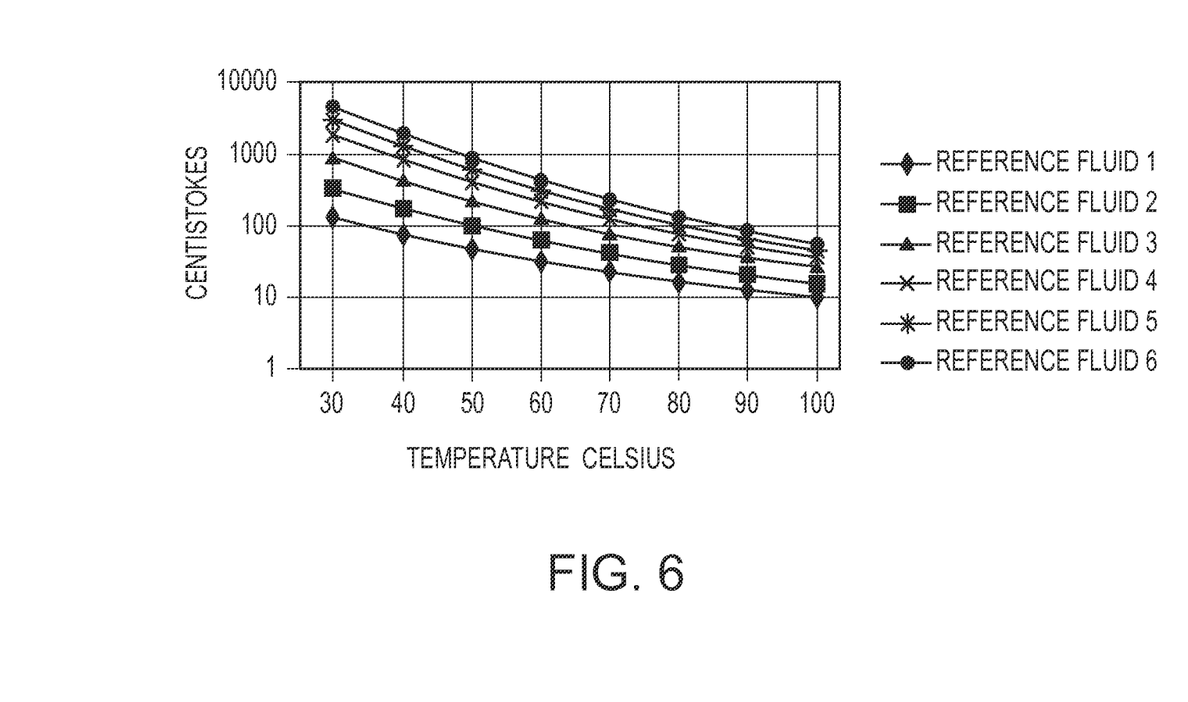
FIG. 6 is a graph of a plurality of reference flow fluid curves that may be used to generate the temperature-viscosity relational data.

FIG. 6 is a graph of a plurality of reference flow fluid curves that may be used to generate the temperature-viscosity relational data. In this example, reference flow fluid curves are shown for six reference flow fluids. The plurality of reference flow fluid curves may comprise the curves generated through iteration of the steps 501 and 502 above, for example. Each of the curves reflects a viscosity value in centiStokes (cSt) over a range of temperatures for a particular flow fluid. The range of temperatures in the graph is from 30 to 100 degrees Celsius, but it should be understood that other temperature ranges may be employed.

Referring again to FIG. 5, in step 504 a desired polynomial order is determined, where the temperature-viscosity relational data is intended to comprise a temperature-viscosity relational polynomial equation. The order may comprise a number that is one less than the number N of reference flow fluids, i.e., the order of the polynomial can range from one up to (N−1). The chosen polynomial order may be stored for subsequent use in generating a representative curve (i.e., generating temperature-viscosity relational data).

The polynomial order may be chosen by a flowmeter designer in some embodiments. Alternatively, in other embodiments the polynomial order may be selected by a flowmeter technician or operator, where the technician or operator may have the knowledge and/or experience to make a proper selection. In another alternative, the flowmeter designer may choose the polynomial order (i.e., a default polynomial order) and the technician or operator may modify the order, such as based on a field accuracy of the vibratory sensor 5 or a desired accuracy.

The order of the polynomial equation may be related to the number of flow fluids being used as references, but the polynomial order is not necessarily the same as the number of reference flow fluids. Where the input data is accurate, a higher order fit will generally result in lower residual errors in the produced reference temperature viscosity values.

However, in some embodiments, the data set may be over-determined. In an over-determined system, the system can produce sets of equations in which there are more equations than unknowns. In the case of an over-determined system, the curve-fitting process may use a lower order fit than mathematically possible in order to minimize ringing or other artifacts that may occur with a higher order curve-fitting process. Alternatively, or in addition, a lower order may be chosen in order to reduce the requisite processing time.

A least squares method is a standard approach to the approximate solution of over-determined systems. A least squares solution minimizes the sum of the squares of the errors made in the results of every single equation.

In some embodiments, the flowmeter designer sets a default polynomial order. The subsequent polynomial equation (or equivalent data structure) is programmed into the vibratory sensor 5. However, in some embodiments, a user can change the default polynomial order, such as based on the accuracy of the results.

Figure 7:
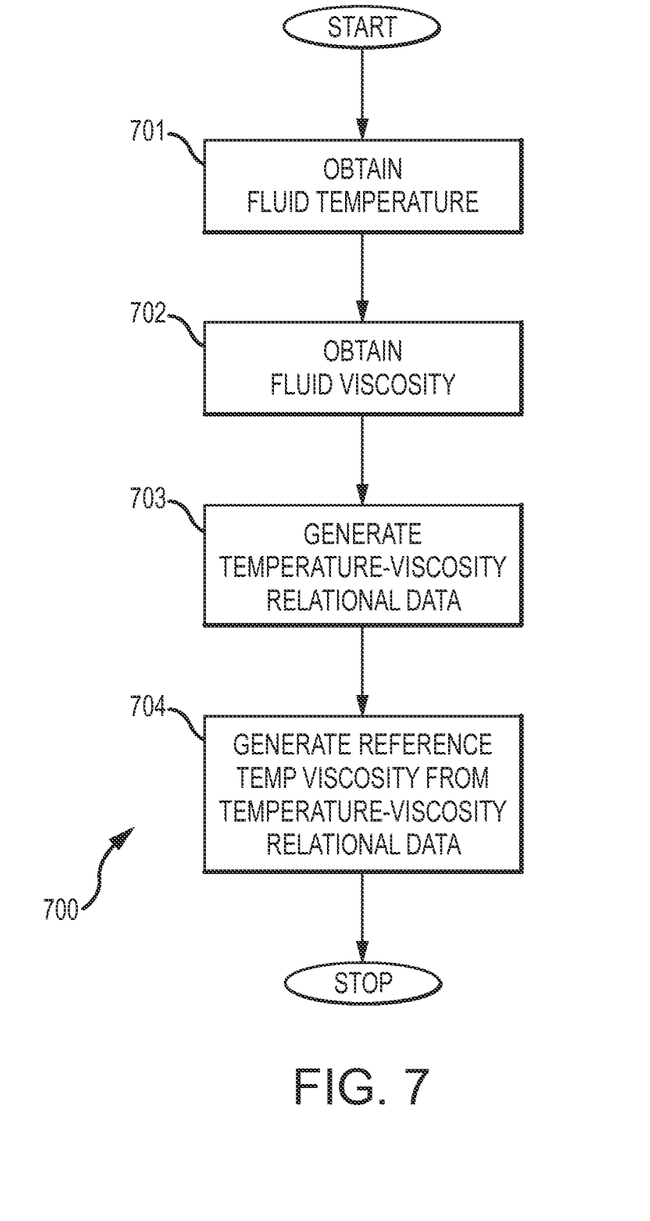
FIG. 7 is a flowchart of a method of obtaining a flow fluid viscosity at a predetermined reference temperature according to an embodiment of the invention.

FIG. 7 is a flowchart 700 of a method of obtaining a flow fluid viscosity at a predetermined reference temperature according to an embodiment of the invention. In step 701, a fluid temperature is measured for the current flow fluid. The fluid temperature measurement can be directly measured or indirectly obtained. The fluid temperature measurement can comprise a temperature measurement obtained from a flow-tube or other structure or component of a vibratory sensor or other sensor. Alternatively, the temperature measurement can be obtained from a source that is external to the vibratory sensor 5.

In step 702, a fluid viscosity is measured for the current flow fluid. The fluid viscosity measurement can be directly measured or indirectly obtained, as discussed above. The fluid viscosity measurement comprises the measured viscosity of the flow fluid at the measured temperature.

Viscosity measurement may be performed in any manner. In some embodiments, the viscosity measurement is obtained using at least a vibratory sensor 5, such as a vibratory tine sensor or a vibratory conduit sensor, for example. The vibratory sensor 5 can determine the flow fluid viscosity alone, or can determine flow fluid viscosity in conjunction with other measuring devices and other measurements.

Viscosity measurement performed using a vibratory flowmeter is disclosed in U.S. Pat. No. 5,661,232 to Van Cleve et al, and is incorporated by reference herein in its entirety. In this arrangement, two Coriolis mass flow meters are used to measure two different flow portions having different resistances to fluid flow. The two meters measure the flow velocities of the two flows, along with measuring two mass flow rates and two densities. A viscosity of the flow fluid can be derived from the fluid flow velocities, fluid flow mass flow rates, and fluid densities.

In step 703, a polynomial equation of the predetermined order is generated from the set of two or more reference flow fluid curves. The polynomial equation may comprise a non-linear equation that more precisely fits the sample data. All of the flow fluid curves in the set of two or more flow fluid curves are used for generating the polynomial equation, even where a relatively low order is chosen for the polynomial equation. The resulting polynomial equation comprises a representative curve, i.e., the representative curve comprises the temperature-viscosity relational data. The temperature-viscosity relational data relates the viscosity at the measured temperature to a viscosity at the specified reference temperature.

This step may include requesting, recalling, or otherwise obtaining a predetermined reference temperature. The reference temperature may comprise a default or standard temperature that is programmed into and stored by the vibratory sensor 5 or stored by the meter electronics 20. Alternatively, the reference temperature may be entered into the vibratory sensor 5 or meter electronics 20 as needed by a technician or operator.

The temperature-viscosity relational data can comprise any suitable relational data. The temperature-viscosity relational data can be in any suitable form.

In some embodiments, the temperature-viscosity relational data may comprise a polynomial equation, where the temperature measurement and the viscosity measurement comprise inputs into the polynomial equation. The polynomial equation outputs a reference temperature viscosity at a predetermined reference temperature.

An appropriate curve-fitting technique may be used to generate the representative curve from the set of two or more flow fluid curves. In some embodiments, a polynomial regression curve-fitting technique may be used to generate the representative curve.

Alternatively, the temperature-viscosity relational data can be converted into a corresponding digital data structure, wherein the temperature-viscosity relational data can be stored and accessed in digital form. The digital data structure can be stored in a computer or other digital device and can be accessed when needed. The digital data structure storing the temperature-viscosity relational data can receive a measured viscosity input and can subsequently generate and output a reference temperature viscosity value. Such a digital data structure can essentially duplicate the function of the polynomial equation, wherein the measured viscosity value may be inputted into a table, for example, and the table outputs a viscosity value for the reference temperature.

The use of the digital data structure to generate a reference temperature viscosity output may include interpolation between stored data points, wherein the produced value falls within the scope or range of the stored data points. The use of the digital data structure to generate a reference temperature viscosity output may include extrapolation between stored data points, wherein the produced value falls outside of or beyond the scope of the stored data points.

The temperature-viscosity relational data may be generated at any appropriate time. The generation of the temperature-viscosity relational data may depend on flow fluid conditions and/or vibratory sensor conditions. The temperature-viscosity relational data may be generated as needed, wherein the vibratory sensor can process the two or more reference flow fluid curves and generate a temperature-viscosity relational data, using the predetermined polynomial order. The temperature-viscosity relational data may be generated in advance of operation of the vibratory sensor or in advance of a need for the temperature-viscosity relational data. The temperature-viscosity relational data may be generated when the measured fluid temperature changes, or when the measured fluid temperature changes significantly (i.e., if the measured fluid temperature deviates from the implicit measured temperature of the temperature-viscosity relational data by more than a predetermined amount). Alternatively, the representative curve may be generated, re-generated, or refined as needed.

In step 704, a reference temperature viscosity is generated using the temperature-viscosity relational data. The measured fluid viscosity is inputted into the temperature-viscosity relational data. A reference temperature viscosity (i.e., a viscosity value for the flow fluid if the flow fluid had been at the reference temperature) is thereby generated by the temperature-viscosity relational data.

The viscosity at the reference temperature may be useful for determining a quality of the flow fluid. The viscosity at the reference temperature may be useful for determining a purity of the flow fluid.

Figure 8:
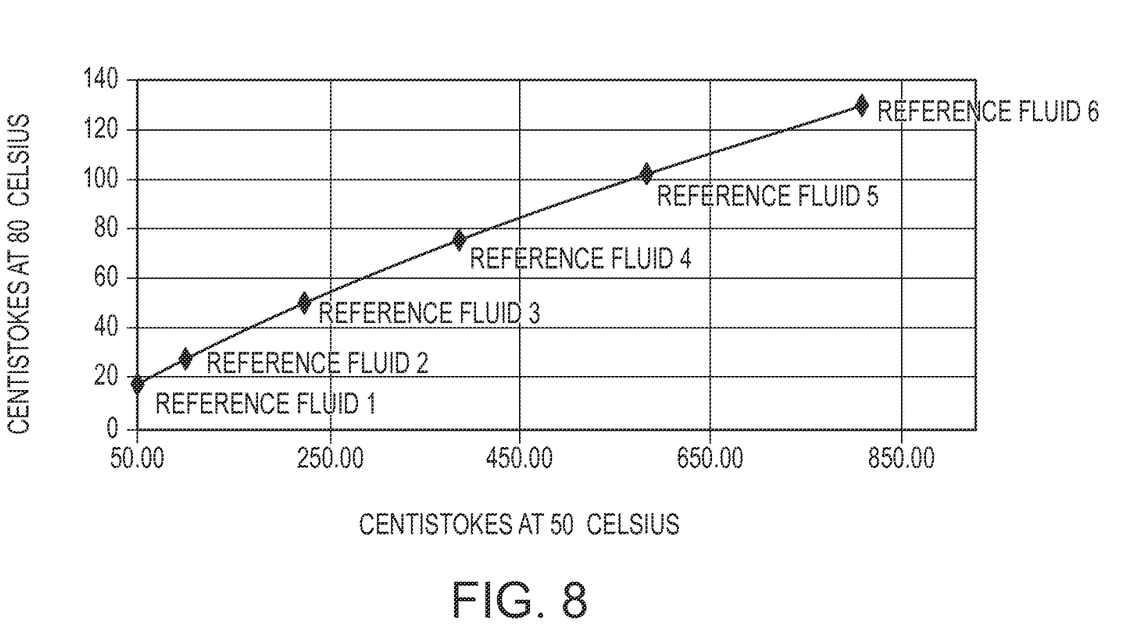
FIG. 8 shows an example of a curve fit of viscosity at two different temperatures.

FIG. 8 shows an example of a curve fit of viscosity at two different temperatures. The vertical axis characterizes the fluid's viscosity in centiStokes and at a fluid temperature of 80 degrees Celsius. The vertical axis characterizes the fluid's viscosity in centiStokes and at a fluid temperature of 50 degrees Celsius.

In this example, the measured process temperature is 50 degrees and the desired reference temperature at which the viscosity is desired to be calculated is 80 degrees (i.e., the predetermined reference temperature is 80 degrees Celsius).

By analyzing the viscosity of the reference fluids one through six, it is determined that a third-order equation may best fit the data (i.e., the predetermined polynomial order is three):

$$y = a_3 x^3 + a_2 x^2 + a_1 x + a_0 \qquad (1)$$

In this example, the x term is the input value, i.e., the measured viscosity at 50 degrees Celsius. In contrast, the y term is the output value and is the reference temperature viscosity at a reference temperature of 80 degrees Celsius. The y term comprises the unknown that will be solved for using the equation in order to generate the reference temperature viscosity. In this example, the $a_0$ term is +6.0863, the $a_1$ term is +0.2307, the $a_2$ term is −0.0002, the $a_3$ term is +7E-08.

In operation, the process receives signals indicating viscosity from a vibrating sensor. The signals are then used to calculate the viscosity of the process fluid in a conventional manner. The calculated viscosity at measured temperature is then inserted into Equation (1) as the x term, wherein Equation (1) has been generated to relate the measured fluid temperature to a predetermined reference temperature. Equation (1) is solved for the y term, which is a viscosity value at the desired reference temperature of 80 degrees Celsius.

The meter electronics and method for obtaining a flow fluid viscosity at a predetermined reference temperature according to the invention can be employed according to any of the embodiments in order to provide several advantages, if desired.

Advantageously, only a single viscometer is needed to measure viscosity at multiple temperatures. Use of a single viscometer enables easier installation. A single viscometer enables quicker measurement responses. A single viscometer enables the measurement of a wider applicable range of fluid viscosities.

Advantageously, there is no particular restriction on application of the method regarding the viscosity range or the characteristics of the process fluids. More particularly, the meter electronics and method may include fluids in addition to petroleum oil or liquid hydrocarbon mixtures, where the ASTM standard has more constraints.

Advantageously, the viscosity calculation is more accurate than other systems. Non-linear equations more precisely fit the sample data, and are used to determine viscosity at other temperatures.

The resulting viscosity measurement at the reference temperature may provide a more accurate measurement of fluid properties, even if those properties vary throughout a batch. The resulting viscosity measurement at the reference temperature may provide a viscosity value that is independent of ambient temperature. The resulting viscosity measurement at the reference temperature may provide a viscosity value that is essentially standardized.

The detailed descriptions of the above embodiments are not exhaustive descriptions of all embodiments contemplated by the inventors to be within the scope of the invention. Indeed, persons skilled in the art will recognize that certain elements of the above-described embodiments may variously be combined or eliminated to create further embodiments, and such further embodiments fall within the scope and teachings of the invention. It will also be apparent to those of ordinary skill in the art that the above-described embodiments may be combined in whole or in part to create additional embodiments within the scope and teachings of the invention. Accordingly, the scope of the invention should be determined from the following claims.

What is claimed is:

1. Meter electronics (20) for obtaining a flow fluid viscosity of a flow fluid at a predetermined reference temperature, with the meter electronics (20) comprising:
   an interface (201) configured to receive sensor signals from a meter assembly (10);
   a storage system (204) configured to store a predetermined reference temperature (211), a measured fluid viscosity (214) measured with the meter assembly (10), a measured fluid temperature (215), and a temperature-viscosity relational data (218) that relates temperature to viscosity over a predetermined range of flow fluid temperatures of the flow fluid; and
   a processing system (203) coupled to the interface (201) and to the storage system (204), with the processing system (203) configured to obtain the measured fluid temperature (215), obtain the measured fluid viscosity (214), and generate a reference temperature viscosity (227) using the measured fluid viscosity (214) and the temperature-viscosity relational data (218), with the generated reference temperature viscosity (227) corresponding to the predetermined reference temperature (211);
   wherein the processing system (203) is configured to create the temperature-viscosity relational data (218) from two or more flow fluid curves (221), the measured fluid temperature (215), the predetermined reference temperature (211), wherein the flow fluid curves (221) reflect temperature-viscosity relationships for two or more reference flow fluids.

2. The meter electronics (20) of claim 1, wherein the temperature-viscosity relational data (218) relates temperature to viscosity for two or more flow fluids over a predetermined range of flow fluid temperatures.

3. The meter electronics (20) of claim 1, wherein one or both of the measured fluid viscosity (214) and the measured fluid temperature (215) are obtained using a vibratory sensor (5).

4. The meter electronics (20) of claim 1, with the temperature-viscosity relational data (218) comprising a polynomial equation.

5. The meter electronics (20) of claim 1, with the temperature-viscosity relational data (218) comprising a polynomial equation of a predetermined polynomial order (223).

6. The meter electronics (20) of claim 1, wherein the temperature-viscosity relational data (218) comprises a relational expression stored as a mathematical equation.

7. The meter electronics (20) of claim 1, wherein the temperature-viscosity relational data (218) comprises a relational expression stored as a data structure.

8. The meter electronics (20) of claim 1, with the storage system (204) storing two or more reference flow fluid curves (221) and a predetermined polynomial order (223), with the processing system (203) being configured to obtain the predetermined polynomial order (223) and create the temperature-viscosity relational data (218) from the predetermined polynomial order (223).

9. A method of obtaining a flow fluid viscosity of a flow fluid at a predetermined reference temperature, the method comprising:
   obtaining a measured fluid temperature of the flow fluid;
   obtaining a measured fluid viscosity of the flow fluid measured with a meter assembly; and
   generating with a meter electronics a reference temperature viscosity using the measured fluid viscosity and a temperature-viscosity relational data that relates temperature to viscosity over a predetermined range of flow fluid temperatures, with the generated reference temperature viscosity corresponding to the predetermined reference temperature;
   wherein the temperature-viscosity relational data is created from two or more flow fluid curves, the measured fluid temperature, and the predetermined reference temperature, wherein the flow fluid curves reflect a temperature-viscosity relationship for two or more reference flow fluids.

10. The method of claim 9, wherein the temperature-viscosity relational data relates temperature to viscosity for two or more flow fluids over a predetermined range of flow fluid temperatures.

11. The method of claim 9, wherein one or both of the measured fluid viscosity and the measured fluid temperature are obtained using a vibratory sensor.

12. The method of claim 9, with the temperature-viscosity relational data comprising a polynomial equation.

13. The method of claim 9, with the temperature-viscosity relational data comprising a polynomial equation of a predetermined polynomial order.

14. The method of claim 9, wherein the temperature-viscosity relational data comprises a relational expression stored as a mathematical equation.

15. The method of claim 9, wherein the temperature-viscosity relational data comprises a relational expression stored as a data structure.

16. The method of claim 9, wherein the temperature-viscosity relational data is generated from two or more reference flow fluid curves using curve fitting.

17. The method of claim 9, further comprising the preliminary steps of:

obtaining a predetermined polynomial order to be used; and creating the temperature-viscosity relational data from the predetermined polynomial order.

18. The method of claim 9, further comprising the preliminary steps of:

measuring viscosity of a particular flow fluid at two or more temperatures to create two or more temperature-viscosity data points for the particular flow fluid; and processing two or more flow fluids and accumulating a plurality of temperature-viscosity data points for the two or more flow fluids to create the two or more flow fluid curves.

* * * * *